United States Patent [19]
Gardini et al.

[11] 4,225,714
[45] Sep. 30, 1980

[54] PROCESS FOR PREPARING P-CHLOROPHENOXY-ACETYL-PIPERONYLPIPERAZINE HYDROCHLORIDE

[75] Inventors: Gian P. Gardini, Parma; Giancarlo Scapini, Bologna; Armando Raimondi, Anagni; Placido Poidomani, Rome, all of Italy

[73] Assignee: Farmaceutici Geymonat Sud S.p.A., Anagni, Italy

[21] Appl. No.: 34,041

[22] Filed: Apr. 27, 1979

[30] Foreign Application Priority Data

Apr. 27, 1978 [IT] Italy ................................ 67952 A/78

[51] Int. Cl.$^2$ ............................................ C07D 405/06
[52] U.S. Cl. .................................................... 544/377
[58] Field of Search ................................ 544/377, 403

[56] References Cited

U.S. PATENT DOCUMENTS

| 3,119,826 | 1/1964 | Regnier et al. | 544/377 |
| 3,523,120 | 8/1970 | Beregi et al. | 544/377 |

FOREIGN PATENT DOCUMENTS 7524M 12/1969 France.

*Primary Examiner*—Paul M. Coughlan, Jr.
*Attorney, Agent, or Firm*—Sughrue, Rothwell, Mion, Zinn and Macpeak

[57] ABSTRACT

The subject compound, otherwise known as Fipexidum hydrochloride, is obtained by reacting the chloride of p-chlorophenoxyacetic acid with 1,4-bis-piperonylpiperazine, preferably in benzene solution under reflux conditions in the presence of a base such as sodium bicarbonate. The advantages of the process are low cost and high overall conversion due to easy recovery and recycle of relevant substances.

7 Claims, No Drawings

PROCESS FOR PREPARING P-CHLOROPHENOXY-ACETYL-PIPERONYLPIPERAZINE HYDROCHLORIDE

The present invention relates to the preparation of p-chlorophenoxy-acetyl-piperonylpiperazine hydrochloride, otherwise known as Fipexidum hydrochloride.

Fipexidum hydrochloride is a psycho-pharmaceutical with an anti-depressant and tonic activity, useful for psychical and physical asthenia. This drug is described in the French Pat. No. 7524. M, and, according to this patent, can be obtained by condensation of piperonyl piperazine (II) with the chloride of p-chlorophenoxyacetic acid (III) in the presence of an equivalent of pyridine in dioxane under reflux conditions, according to the reaction:

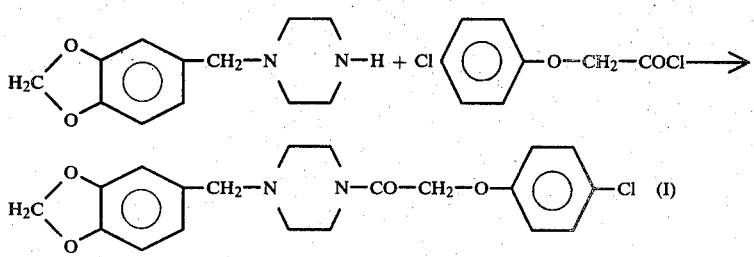

The product (I) is isolated in the form of the hydrochloride, with a yield of 61%, and has a melting point (Kofler) of 230°–232° C.

The major disadvantage of this particular synthesis resides in the high production cost (or market price) of piperonylpiperazine (II). In fact, this latter is prepared from piperazine and piperonyl chloride by refluxing in methanol for about 90 minutes, followed by fractional distillation under high vacuum (2 mm Hg), with a stated yield of 35% (Belgium Pat. No. 616,371). This low yield and the difficulty of obtaining the compound (II) in the pure state have a strong influence on the production costs of Fipexidum hydrochloride.

According to the present invention, Fipexidum hydrochloride is obtained by reacting the chloride of p-chlorophenoxyacetic acid with 1,4-bis-piperonylpiperazine, particularly in an organic solvent and in the presence of a base. The solvent is preferably benzene and the base is preferably sodium bicarbonate, and the reaction is carried out by heating under reflux. The synthesis scheme according to the invention is as follows:

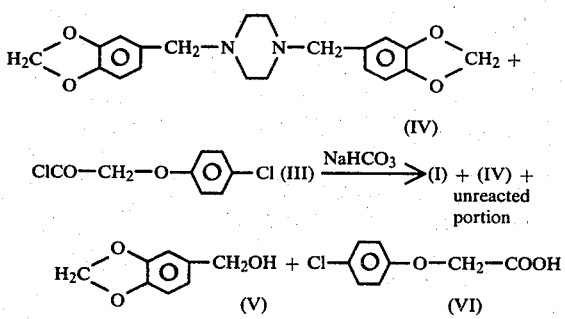

The Fipexidum hydrochloride is easily obtained from the reaction mixture in the form of the hydrochloride with a yield of the order of 55%. This yield is less than the 61% obtainable according to the French Patent cited above, but this disadvantage is in practice negligible in comparison with the following advantages:

(a) In place of the costly piperonylpiperazine (II), there 1,4-bis-piperonylpiperazine (IV) is used, which can be prepared at low cost from piperazine and piperonyl chloride under micellary catalysis conditions with the use of a suitable surfactant, a process which is the subject of Ser. No. 34,040 filed Apr. 27, 1979 by the same applicants, entitled "Process for preparing 1,4-bis-piperonylpiperazine and similar compounds" (Case I).

(b) All the by-products of the reaction are easily recoverable in high yields and reusable, as will be shown below. By this means, in particular, the total conversion yield of the 1,4-bis-piperonylpiperazine exceeds 90%.

The process of the present invention thus becomes particularly interesting if it is used in combination with the process for the preparation of 1,4-bis-piperonylpiperazine according to the aforesaid Ser. No. 34,040 Application of the same date, as will be seen from the following embodiment given by way of example.

EXAMPLE (A) Preparation of 1,4-bis-piperonylpiperazine 25.8 g (0.3 moles) of anhydrous piperazine and 32.5 ml (1.8 moles) of distilled water (or simply 58.3 g (0.3 moles) of piperazine hexahydrate) are loaded into a 250 ml flask provided with an agitator, a thermometer and a reflux condenser, together with 51.2 g (0.3 moles) of piperonyl chloride, whereupon 2 g of cetyl-trimethylammonium bromide are added to the mixture with vigorous agitation, and the flask is cooled with water so that the temperature of the reaction mass under agitation does not rise above 110° C. Once the exothermic stage is exhausted, the temperature is maintained at 130° C.±5° C. by an external oil bath, for 90 minutes, under agitation.

After cooling, a solid mass is obtained which is taken up with 400 ml of an aqueous solution containing 10% by weight of caustic soda to dissolve the product from the mass. The alkaline solution thus obtained is extracted twice with 500 ml of chloroform. The extract is washed with water and then evaporated to dryness. The residue is crystallised from 96% ethanol.

50.5 g (theoretical value 53.18 g) of a pale-yellowish white crystals are obtained with a melting point of 155°–156° C. The yield is 95% of the theoretical. In accordance with the Belgian Patent cited above, the di-hydrochloride melts with decomposition above 260° C.

Analysis for $C_{20}H_{22}N_2O_4$: Calc. %: C,67.78; H,6.26; N,7.90. Found %: C,67.52; H,6.25; N,7.97.

(B) Preparation of Fipexidum hydrochloride 106.3 g (0.3 moles) of 1,4-bis-piperonylpiperazine are dissolved in 750 ml of hot benzene in a 2,000 ml flask provided with a stirrer and a reflux condenser and 38 g (0.45 moles) of dry, powdered sodium bicarbonate are added. After cooling to ambient temperature, 92.3 g (0.45 moles, corresponding to 63 ml) of the chloride of p-chlorophenoxyacetic acid are added slowly, with agitation, and the mixture is heated under reflux for 7 hours. The benzene is then almost totally recovered by distillation at atmospheric pressure and the residue is evaporated to dryness under vacuum. The solid residue thus obtained is taken up with 400 ml of aqueous solution at 10% sodium hydroxide (1mole) and the alkaline liquid phase is extracted twice with 600 ml of chloroform. The chloroform extracts are joined together and washed with a little water and then agitated vigorously with a solution of 200 ml of concentrated hydrochloric acid in 300 ml of water. An abundant white precipitate is obtained consisting of a mixture of the hydrochloride of compound (I) and the di-hydrochloride of the unreacted amount of compound (IV). After filtration under vacuum, the precipitate is treated with boiling ethanol 96% strength; the Fipexidum hydrochloride passes into solution while the di-hydrochloride of compound (IV) remains undissolved and is separated by filtration while hot. The alcoholic filtrate is cooled, with consequent slow crystallisation of the Fipexidum hydrochloride (I). 70.2 g of the product are obtained with a yield of 55%; melting point (in Kofler) 228°–230° C.

Analysis for $C_{20}H_{22}Cl_2N_2O_4$: Calc. %: C,56.48; H,5.21; N,6.58. Found. %: C,56.72; H,5.28; N,6.45.

(C) Recovery of unreacted 1,4-bis-piperonylpiperazine

As described above, di-hydrochloride of unreacted amount of compound (IV) remains as a residue from the treatment with boiling ethanol. This residue is taken up with 200 ml of aqueous sodium hydroxide at 10% concentration and the obtained alkaline solution is extracted twice with 50 ml of chloroform. The chloroform extract is washed with water, then dried on anhydrous sodium sulphate, and evaporated to dryness. 42 g of compound (IV) are obtained (90% of the theoretical); melting point 153°–155° C. Without further purification, this reagent is reused in stage (B) for the production of further quantities of Fipexidum hydrochloride.

(D) Recovery of the piperonyl alcohol (V)

The chloroform filtrate remaining after the precipitation with hydrochloric acid of the hydrochlorides of compounds (I) and (IV) in stage (B) described above, contains piperonyl alcohol (V). This filtrate is washed with water to eliminate HCl, then evaporated to a small volume with recovery of the chloroform, and then brought to dryness under vacuum. By crystallisation of the residue from ligroin, 21.3 g (85% of the theoretical) of piperonyl alcohol (V) are recovered and converted to chloride by treatment with gaseous hydrogen chloride, as described in the Journal of Organic Chemistry 31, 1090 (1966). The chloride of compound (V) obtained in this manner is reused in stage (A) for the reaction with piperazine.

(E) Recovery of the p-chlorophenoxyacetic acid (VI)

The aqueous alkaline phase remaining from stage (B) after the extraction with chloroform is acidified with concentrated hydrochloric acid and then left quiescent. 45.7 g (86% of the theoretical) of the acid (VI) crystallise slowly: m.p. 154°–156° C. After conversion to chloride (III) by treatment with $SOCl_2$ as described in J.A.C.S. 53,304 (1931), the product obtained is reused in stage (B) described above.

We claim:

1. A process for the synthesis of p-chlorophenoxyacetyl-piperonylpiperazine hydrochloride (I), which comprises reacting substantially pure 1,4-bis-piperonylpiperazine with the chloride of p-chlorophenoxyacetic acid.

2. A process according to claim 1, in which the reaction is carried out in an organic solvent in the presence of a base.

3. A process according to claim 2, in which the solvent is benzene and the base is sodium bicarbonate.

4. A process according to any one of claims 1 to 3, in which the reaction is carried out by heating under reflux.

5. A process according to claim 1, wherein the reaction is carried out in an organic solvent in the presence of a base and further including the steps of:
   (a) at the end of the reaction, evaporating the reaction mass to dryness;
   (b) adding aqueous sodium hydroxide to the residue to obtain an alkaline solution;
   (c) extracting the p-chlorophenoxyacetyl-piperonylpiperazine from the solution with an organic solvent;
   (d) precipitating the hydrochloride (I) from the extract, together with the di-hydrochloride of the unreacted portion of 1,4-bis-piperonylpiperazine, by adding aqueous hydrochloric acid, and recovering the precipitate;
   (e) separating the hydrochloride (I) from the precipitate by treating the precipitate with a solvent selective for the hydrochloride (I), filtering the mixture to obtain a solid residue and a filtrate containing the hydrochloride (I), and crystallizing the latter from the filtrate.

6. A process according to claim 5, wherein:
   (f) unreacted 1,4-bis-piperonylpiperazine is recovered from the solid residue of step (e) by treatment of the residue with aqueous alkali and extraction of the aqueous alkaline solution with a volatile solvent for the 1,4-bis-piperonylpiperazine;
   (g) piperonyl alcohol formed as by-product in the reaction of claim 1 is recovered from the liquid phase obtained in step (d) by washing the liquid phase with water and concentrating the washed phase to dryness;
   (h) p-chlorophenoxyacetic acid formed as by-product in the reaction of claim 1 is recovered from the aqueous alkaline phase remaining from extraction step (c) by acidification of the latter phase and crystallization from the acidified phase.

7. A process for the synthesis of p-chlorophenoxyacetal-piperonylpiperazine hydrochloride (I), which comprises reacting substantially pure 1,4-bis-piperonylpiperazine with an equimolar amount or an excess of the chloride of p-chlorophenoxyacetic acid.

* * * * *